US012788021B2

(12) United States Patent
Raghubeer

(10) Patent No.: US 12,788,021 B2
(45) Date of Patent: Nov. 10, 2026

(54) HIGH PRESSURE PROCESSING FOR PERSONAL PROTECTIVE EQUIPMENT AND LOW MOISTURE FOODS

(71) Applicant: AVURE TECHNOLOGIES INCORPORATED, Middleton, OH (US)

(72) Inventor: Errol V. Raghubeer, Federal Way, WA (US)

(73) Assignee: JBT Marel Corporation, Chicago, IL (US)

( * ) Notice: Subject to any disclaimer, the term of this patent is extended or adjusted under 35 U.S.C. 154(b) by 950 days.

(21) Appl. No.: 18/001,404

(22) PCT Filed: Jun. 7, 2021

(86) PCT No.: PCT/US2021/036122
§ 371 (c)(1),
(2) Date: Dec. 9, 2022

(87) PCT Pub. No.: WO2021/252332
PCT Pub. Date: Dec. 16, 2021

(65) Prior Publication Data
US 2023/0217966 A1 Jul. 13, 2023

Related U.S. Application Data

(60) Provisional application No. 63/036,628, filed on Jun. 9, 2020.

(51) Int. Cl.
*A23L 3/015* (2006.01)
*A23B 2/10* (2025.01)
(Continued)

(52) U.S. Cl.
CPC .............. *A23B 2/103* (2025.01); *A23B 2/708* (2025.01); *A23B 2/721* (2025.01); *A61L 2/02* (2013.01); *A61L 2/22* (2013.01); *A61L 2202/122* (2013.01)

(58) Field of Classification Search
CPC ........... A23B 2/003; A23B 2/10; A23B 2/103; A23B 2/30; A23B 2/708; A23B 2/721;
(Continued)

(56) References Cited

U.S. PATENT DOCUMENTS

| | | | |
|---|---|---|---|
| 2002/0020462 | A1 | 2/2002 | Wagenheim |
| 2003/0017035 | A1 | 1/2003 | Solomon et al. |

(Continued)

FOREIGN PATENT DOCUMENTS

| | | | |
|---|---|---|---|
| CN | 111093385 | A | 5/2020 |
| KR | 20110118521 | A | 10/2011 |

(Continued)

OTHER PUBLICATIONS

Office Action and Search Report mailed Mar. 29, 2025, issued in corresponding Chinese Application No. 202180041754.X , filed Jun. 7, 2021, 22 pages.

(Continued)

*Primary Examiner* — Hung D Nguyen
(74) *Attorney, Agent, or Firm* — Christensen O'Connor Johnson Kindness PLLC

(57) ABSTRACT

A high pressure process for decontamination comprises subjecting a hermetically-sealed package containing a product and a gas to an operating pressure by a pressurizing media containing water, wherein the product has a water activity less than or equal to 0.9; increasing the operating pressure to change the gas into a different phase; and maintaining the operating pressure for a sufficient length of time to achieve some decontamination inside the package.

21 Claims, 2 Drawing Sheets

(51) Int. Cl.

| | |
|---|---|
| ***A23B 2/708*** | (2025.01) |
| ***A23B 2/721*** | (2025.01) |
| ***A61L 2/02*** | (2006.01) |
| ***A61L 2/22*** | (2006.01) |

(58) Field of Classification Search

CPC ........ A61L 2/02; A61L 2/22; A61L 2202/122; A23L 3/0155; A23L 3/3418; A23L 3/3445

See application file for complete search history.

(56) References Cited

U.S. PATENT DOCUMENTS

| | | | | |
|---|---|---|---|---|
| 2011/0067355 | A1 | 3/2011 | Richter | |
| 2013/0078339 | A1* | 3/2013 | Trahan ................... | A23B 2/788 426/106 |

FOREIGN PATENT DOCUMENTS

| | | | |
|---|---|---|---|
| TW | 201690843 | A | 3/2016 |
| WO | 2015160269 | A1 | 10/2015 |
| WO | 2019043442 | A1 | 3/2019 |

OTHER PUBLICATIONS

Communication mailed Sep. 8, 2025, issued in corresponding European Patent Application No. 21736134.4, filed Jun. 7, 2021, 6 pages.

International Preliminary Report on Patentability and Written Opinion mailed Dec. 13, 2022, issued in corresponding International Application No. PCT/US2021/036122, filed Jun. 7, 2021, 8 pages.

Communication Pursuant to Article 94(3) EPC mailed Jan. 15, 2025, issued in corresponding Application No. EP 21 736 134.4, filed Jun. 7, 2021, 7 pages.

Office Action mailed May 16, 2025, issued in corresponding Vietnamese Application No. 1-2023-00023, filed Jun. 7, 2021, 4 pages.

Anonymous: "Water activity—Wikipedia", Apr. 21, 2020 (Apr. 21, 2020), pp. 1-7, XP055840966, Retrieved from the Internet: URL:https://en.wikipedia.org/w/index.php?title=Water activity&oldid=952368524 [retrieved-on Sep. 14, 2021] the whole document.

Anonymous: "Water activity and its relevance—Technical information note", Mar. 30, 2017 (Mar. 30, 2017), pp. 1-2, XP055612445, www.dairysafe.vicgov.au/publications-medi a/technical-information-notes/product/409-water-activity/file Retrieved from the Internet: URL:http://web.archive.org/web/20170330053 008if /http://www.dairysafe.vicgov.au/pub licatTons-media/technical-information-note s/product/409-water-activity/file [retrieved on Aug. 13, 2019] the whole document.

Radm Denise M. Hinton: "Letter of Authorization", Aug. 20, 2020 (Aug. 20, 2020), pp. 1-8, XP055841047, Retrieved from the Internet: URL:https://www.fda.gov/media/141382/download [retrieved on Sep. 14, 2021] the whole document.

Novasterilis N: "Nova2200 Equipment Platform for NovaClean decontamination process Instructions for Decontamination Personnel (DP)", 3109 N. Triphammer Rd. Lansing, NY 14882, Aug. 20, 2020 (Aug. 20, 2020), pp. 1-10, XP055841034, Retrieved from the Internet: URL:https://www.fda.gov/media/141386/download [retrieved on Sep. 14, 2021] the whole document.

Bennet Devasier et al: "Evaluation of supercritical CO2 sterilization efficacy for sanitizing personal protective equipment from the coronavirus SARS-CoV-2", Science of the Total Environment, vol. 780, Aug. 1, 2021 (Aug. 1, 2021), p. 146519, XP055840725, Amsterdam, NL ISSN: 0048-9697, DOI: 10.1016/j.scitotenv.2021.146519 abstract.

International Search Report PCT/US2021/036122 Sep. 24, 2021.

Communication Pursuant to Article 94(3) EPC mailed Apr. 29, 2024, issued in corresponding Application No. EP 21 736 134.4, filed Jun. 7, 2021, 6 pages.

Examination Report mailed Jun. 24, 2026, issued in corresponding Vietnamese Patent Application No. 1-2023-00023 filed Jun. 7, 2021, 5 pages.

Second Office Action mailed Nov. 28, 2025, issued in corresponding Chinese Patent Application No. 202180041754.X , filed Jun. 7, 2021, 13 pages.

First Examination Report mailed May 12, 2026, issued in corresponding Australian Patent Application No. 2021286458, filed Jun. 7, 2021, 5 pages.

Examination Report mailed Jun. 9, 2026, issued in corresponding Candadian Patent Application 1 No. 3,184,456, filed Jun. 7, 2021, 7 pages.

* cited by examiner

HIGH PRESSURE PROCESSING FOR PERSONAL PROTECTIVE EQUIPMENT AND LOW MOISTURE FOODS

CROSS-REFERENCE TO RELATED APPLICATION

This patent application is the national phase of International Application No. PCT/US2021/036122, filed on Jun. 7, 2021, which claims priority of US Patent Application No. 63/036,628, filed on Jun. 9, 2020, the entire disclosures of both applications are hereby incorporated by reference herein for all purposes.

BACKGROUND

High pressure processing (HPP) is used to reduce the microbial load on foods, beverages, cosmetics, pharmaceuticals and other products without altering the characteristics of the processed product. The pressure level required for HPP to be successful is typically at least 2,000 bar.

Traditional equipment for treatment of beverages and other liquids as well as pumpable foods and other substances by HPP is based on the processing of the products after having been placed as individual units into flexible packaging, for example, plastic bottles, or pouches. The individual units are grouped or consolidated within a larger reusable load basket which is sized and shaped to fit into a wire wound high pressure vessel (also referred to as “wire wound vessel” or “high pressure vessel”).

Such high pressure vessel is filled with water which serves as the pressurizing medium. Once the wire wound vessel has been closed and filled, high capacity pumps introduce additional water into the pressure vessel so that the pressure therein is increased from about 2,000 to 10,000 bar or higher. This pressure is maintained for a sufficient length of time, from a few seconds to several minutes, to reduce the microbial load on the products being treated. The particular pressure level and the time duration of such pressure are specific to the product being processed based mostly on intrinsic factors such as pH, water activity levels and natural or added ingredients.

Once the desired level of inactivation of the microorganisms has been achieved, the pressure in the vessel is released and the load basket is removed from therein so that the individual packages or units can be extracted. The processed product has, after being exposed to high pressure and hold time, been pasteurized, the microbial load has been reduced, foodborne pathogens and viruses have been eliminated and an extended shelf life has been achieved.

There is a great need to decontaminate personal protective equipment (PPE) material, such as N95 masks, for re-use or possibly for eventual disposal. However, because of the absence of free water in direct contact with these materials, the efficacy of HPP on viral and other microbial entities can be very limited. Accordingly, methods and systems are needed to address this problem.

SUMMARY

According to this disclosure, since PPE cannot be packaged in water, it is proposed herein to use gaseous carbon dioxide ($CO_2$). Additionally, the formation of supercritical $CO_2$ ($sCO_2$) under correct temperature and pressure conditions may contribute to the microbial inactivation process.

HPP of product packaged in gaseous $CO_2$ can provide a solution to the need for decontamination and re-use of N95 masks or other PPE for health care workers and frontline personnel. Additionally, HPP of product packaged in gaseous $CO_2$ can also be used for the inactivation of pathogens for low and intermediate moisture foods.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

High pressure vessels have been commercially available for more than 25 years. They exist in different configurations and sizes. All systems though include a pressure vessel that is able to withstand very high pressure levels. The most common pressure media used is water, but also water with additives may be used.

Figure 1:
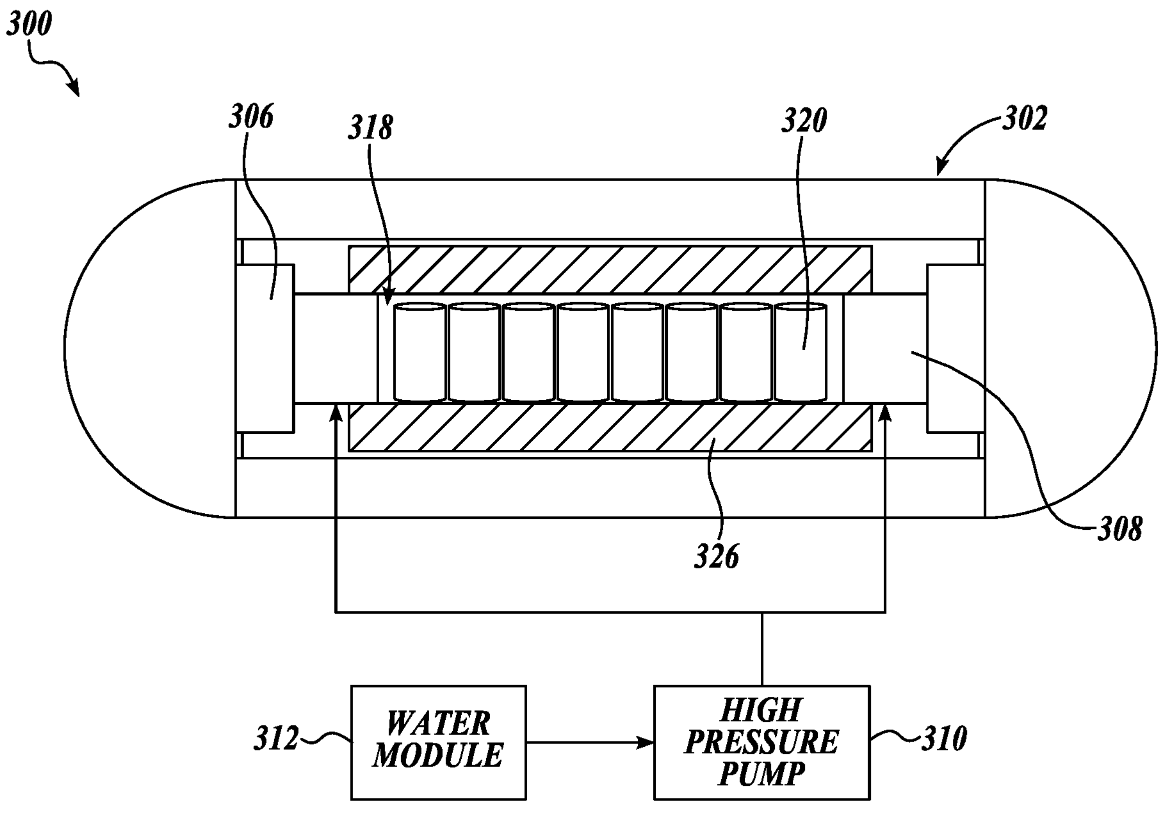
FIG. 1 is a schematic illustration of a high pressure vessel using water as a pressurization media.

Referring to FIG. 1, portions of a high pressure processing (HPP) system 300 are illustrated according to the present disclosure in which packages 320 containing no or low moisture products and carbon dioxide gas will be treated by the high pressure processing system 300. FIG. 1 is merely schematic as other ancillary systems for the operation need not be shown for understanding the disclosure. For example, the high pressure processing system 300 is understood to be equipped with additional pressure media pumping and decompression systems.

A high pressure vessel 326 has a chamber 318 in which the gas-filled packages 320 containing product to be decontaminated are placed. The pressure media, such as water, is pumped into the chamber 318 to fill the chamber 318 and surround the packages 320. The pressure in the chamber 318 is then increased to the operating pressure to provide decontamination through high pressure. In the present disclosure, the operating pressure will also result in a change from the gas to the liquid or supercritical phase within the packages 320, which also functions for decontamination.

The chamber 318 is supported on a frame comprised of a longitudinal frame structure 302. The frame structure is any rigid structure capable of providing the structural functionality for the high pressure processing described herein.

In order to keep the pressure media inside the pressure vessel 326, in one embodiment, there is one closure/plug 306, 308 at each end of the pressure vessel 326. Closures 306, 308 are free floating and will be pushed outwards during pressurization. The closures 306, 308 are held in place with the frame 302 acting as a yoke.

However, the present disclosure can also apply to different pressure vessel designs. For example, the pressure vessel can use different designs of frames/yokes and both wire wound frames as well as plate frames.

The present disclosure also applies to smaller pressure vessels that may omit a frame. In which case, the closures are held in place with another type of locking system, such as a pin closure design, interrupted thread design etc.

The pressure vessel can also use different designs of cylinders and both wire wound cylinders/vessel as well as monolithic cylinder/vessel that are able to withstand the high pressure described in this application.

The high pressure processing system 300 also includes one or more high pressure pump(s) 310, water module(s) 312, electrical cubicle(s) including a programmable logic controller, instrumentation and the communication cables, material handling equipment for loading and unloading product, and auxiliary hydraulic unit(s), for example.

In one embodiment, the water module 312 provides the pressure vessel 326 with water during pre-fill as well as to all high pressure pumps/intensifiers during the pressure level increasing step.

Figure 2:
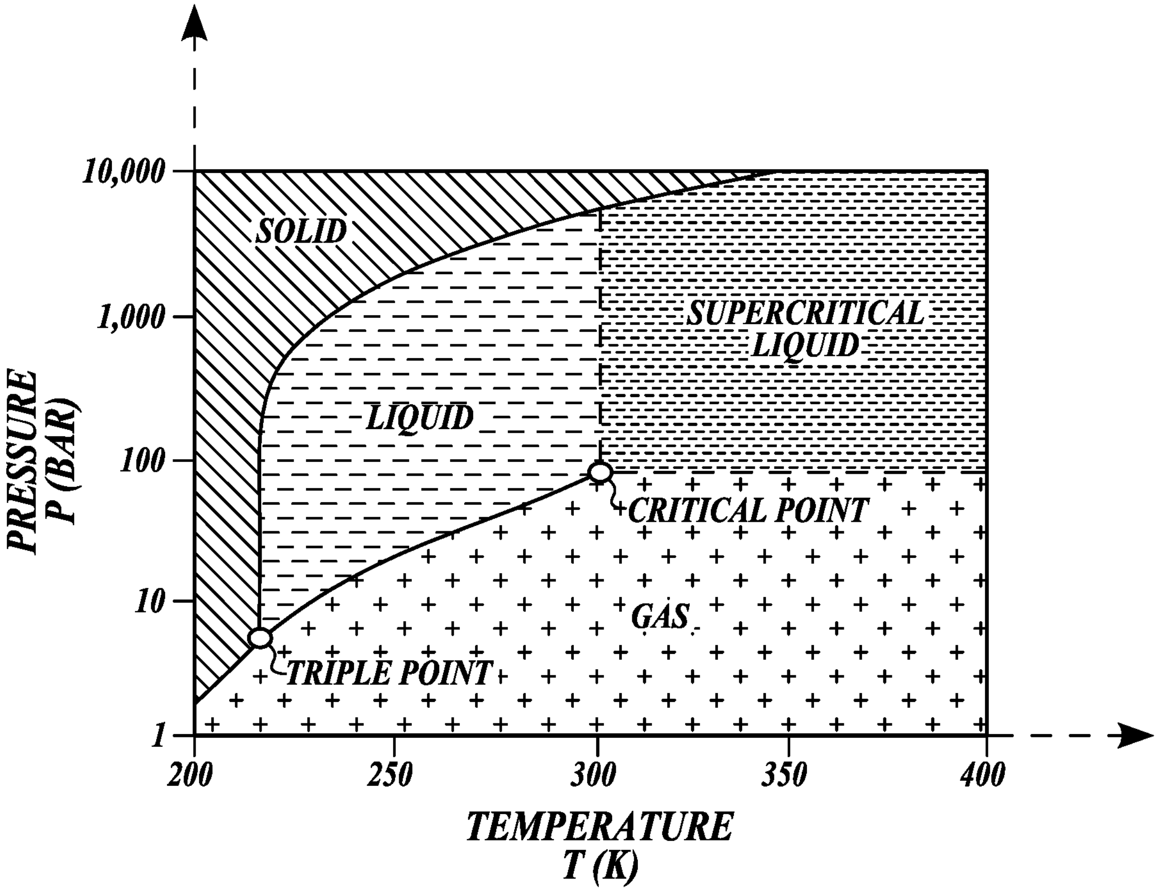
FIG. 2 is a phase diagram of carbon dioxide.

In this disclosure, changing the phase of $CO_2$ or other gas from the gas phase into the liquid or supercritical phase will depend on the temperature as well as the pressure. This means that the pressure and temperature of the $CO_2$ gas inside the packages 320 must intersect in the liquid or supercritical fluid regions of the phase diagram (see FIG. 2).

Conventional HPP pressure vessels can easily operate in the regions of liquid and supercritical fluid as to both temperature and pressure. The temperature needed to achieve supercritical fluid is only 31.1° C. for $CO_2$.

The water module 312 in conventional HPP systems has a heat exchanger that can be used to chill or heat the water pumped into the pressure vessel 326, thereby cooling or heating the gas-filled packages 320. Some conventional HPP pressure vessels 326 will have an internal heater that will also be used to achieve the desired temperature.

Further, when applying pressure, the water experiences an adiabatic temperature rise of about 3° C. per 1,000 bar. This adiabatic temperature rise can also contribute to achieving the desired temperature. The adiabatic temperature rise can be estimated as the operating pressure is known.

Heating the water from the water module 312 may account for the bulk of the heat to increase temperature in the pressure vessel 326. Additionally, since the large mass of the pressure vessel 326 can prevent a rapid increase in temperature, the air temperature of the room in which the pressure vessel 326 is housed can be increased as a way of further heating the pressure vessel 326.

The product in this disclosure can be any dry, low moisture, low water activity ($A_w$) product or material, including PPE, such as N95 face masks. In one embodiment, water activity is a measure of the free (non-chemically bound) water in the product. It can be the value of the partial pressure of water in the product (p) to be decontaminated divided by the standard state partial vapor pressure of pure water ($p_o$): $A_w=p/p_o$.

In one embodiment, the water activity of low moisture foods is less than 0.70. In one embodiment, the water activity of intermediate moisture foods is about 0.70 to about 0.90. In one embodiment, the water activity of dried foods is less than 0.60. The process disclosed herein can be applied to decontamination of food and non-food products, such as PPE, having a water activity generally less than or equal to 0.9.

The packages 320 in this disclosure can be any package, pouch, or container used for containing one or more of the product or materials together with a volume of gas, such as $CO_2$ that can withstand the HPP. In one example, the packages 320 can be made from plastic sleeves (or bags) using materials, such as polyethylene or other waterproof flexible packaging materials. The packages 320 can be hermetically sealed so as to prevent the gas from escaping as well as preventing the water in the pressure vessel to enter the packages.

The packages 320 are flexible to compress when under pressure as the volume of the gas is reduced and converted to liquid or supercritical fluid. In some embodiments, a basket specifically configured for use with HPP equipment can be used to contain a plurality of the hermetically sealed packages, pouches, or containers.

For N95 masks, the packages 320 can be sleeve-shaped. Some N95 masks are collapsible and will lie flat atop each other in a stack. Some N95 masks may be more rigid and cup-shaped which can allow nesting one mask within another. Stacking masks into sleeves can maximize the number of masks per package and also minimizes deformation. Some masks may require disassembly before performing HPP. Once decontaminated, the parts of the masks that are decontaminated may be re-assembled, provided sterility is maintained, with new parts or with parts that are decontaminated separately.

In either case, the N95 masks can be compactly stacked inside of a sleeve-shaped package 320, and then arranged either vertically or horizontally in the chamber 318. In one example, masks can be sorted and stacked manually inside of the packages 320. However, it is contemplated that sorting, stacking, and filling the sleeve-shaped packages 320 with product will eventually be automated.

Once the packages 320 are filled with product, the packages 320 can be loaded into a gas-filling and sealing machine, also referred to as Modified Atmosphere Packaging system. Modified Atmosphere Packaging systems are advanced to the point where the amount of gas that is delivered to each package 320 is controlled by inputting the desired amount on a control panel.

In one example, it is contemplated that a gas-filled package 320 will have a volume of about 25 liters and can hold about 1,000 stacked masks. Conventional HPP pressure vessels have a chamber 318 volume in the range of about 100 to 525 liters. Therefore, even the smaller HPP systems can decontaminate several thousand N95 masks in one processing cycle.

HPP technology has been used for the food and beverage industry to ensure food safety, increase shelf-life and extend product quality. The efficacy of HPP on viral and other microorganisms depends on intrinsic factors in the products under pressure, most importantly on the availability of adequate amount of free water referred to as water activity ($A_w$). In the absence of free water or when $A_w$ is significantly reduced, the efficacy of HPP in microbial inactivation is compromised. The process of this disclosure is the use of HPP for products that have no or low free water or low water activity by introducing gases, such as $CO_2$, into the packages together with the products, and then subjecting the gas-filled packages to an operating pressure and temperature that converts the gas into a liquid or supercritical fluid. The operating pressure is held for a sufficient length of time to achieve decontamination through high pressure.

The efficacy of prior HPP to inactivate microorganisms is dependent on the presence of free water ($A_w$), and when the free water of the product to be decontaminated is low, there is little to no effect on pathogens and spoilage microorganisms. With the use of gases, such as $CO_2$ under pressure, HPP can now be successfully applied to dry/low moisture/low $A_w$ food products as well as non-food materials to inactivate pathogens and other microorganisms.

Gaseous carbon dioxide ($CO_2$) will change to a liquid under pressure at the correct temperature range and pressure.

When moist air is present, some of the liquified $CO_2$ will form carbonic acid. At decompression most of the liquified $CO_2$ will revert back to the gas phase. Either the liquid $CO_2$ by itself or in combination with carbonic acid and the pressure intensity will result in the inaction of viruses and other microorganisms. Additionally, by increasing the temperature above the critical point (31° C.) for gaseous $CO_2$, high pressure will promote the formation of supercritical carbon dioxide ($sCO_2$) which by itself can inactivate viruses and other microorganisms.

In some embodiments, carbon dioxide can be substituted with other "generally recognized as safe" (GRAS) gases. Other GRAS gases that may be used as a substitute for or in combination with carbon dioxide include, but are not limited, air, helium, nitrogen, oxygen, nitrous oxide, propane, hydrogen, carbon monoxide, and argon. To use in embodiments of this disclosure, the gas or gas mixture should undergo a phase change at the operating pressures described herein.

Using HPP that converts $CO_2$ gas in the packages to liquid or supercritical $CO_2$ can effectively decontaminate PPE and inactivate pathogens and other microorganisms in dried/low moisture/low water activity ($A_w$) food products such as, but not limited to, meat jerky, dried/low moisture fruits and vegetables, jams, marmalades, jellies, chocolate, candies, nuts including low moisture coconut products, dried seafood products, salted meat, and seafood, etc.

The capability of using HPP technology with carbon dioxide-filled packages to sterilize or pasteurize dry/low moisture/low $A_w$ food products presents the opportunity for the treatment of food products that are not effectively decontaminated under the current HPP where water in the product is a critical factor for antimicrobial efficacy.

Further, the present disclosure provides a solution to meet the immediate need for a viable decontamination process for re-using PPE to alleviate the shortage of these materials for health care workers and other essential frontline personnel involved in dealing with the SARS-CoV-2 pandemic.

N95 masks are normally considered to be disposable after a single use. However, due to shortages for healthcare and front-line workers, there has been an interest in re-using masks after decontamination. In one embodiment, masks are made from non-woven polypropylene fiber. It is believed that the process of this disclosure can be used for decontamination to any material. Preferably if the material can withstand pressures in the range of about 74 to 6,000 bar or higher, the material can be treated with supercritical $CO_2$. Other PPE that may be considered single-use only and disposable, may also be processed according to this disclosure. Such PPE may include plastic face shields, gowns, shoe coverings, full body suits, and gloves. However, PPE does not need to be designated single use or disposable to be decontaminated according to the disclosed process.

Gaseous $CO_2$ transitions to the liquid phase at pressures above 5.2 bar within a temperature range of −56.6 to 31.1° C. When moisture is present, such as in high humidity air, the pressurization of $CO_2$ will also produce some amount of carbonic acid within the critical temperature limits. Above 31.1° C. and greater than 73.8 bar, $CO_2$ is a supercritical fluid ($sCO_2$) where it expands in the package like a gas, but with the density of a liquid. These changes may have antimicrobial properties and functional properties that can preserve the integrity of products and packaging materials in dried (low moisture) foods. The transition states of $CO_2$ at various pressures and temperatures are shown in the $CO_2$ phase diagram in FIG. 2.

$CO_2$, as well as a number of other gases, are commonly used in the food industry, and have no toxic or harmful effects to humans. The presence of gases, such as $CO_2$, in packages subjected to HPP may be effective to achieve decontamination in products with low water activity when the combination of operating temperature and pressure is in the $CO_2$ liquid and supercritical phase. Preferably, the operating pressure is from 690 bar to 6,000 bar or greater, and the operating temperature is any temperature intersecting the pressure in the liquid or supercritical fluid region. Preferably, the temperature can be from −20° C. to 35° C. In one embodiment, the pressure may be greater than 6,000 bar, such as a pressure up to 10,000 bar. In one embodiment, the temperature may be greater than 35° C., such as up to 65° C. In one embodiment the hold time at the operating pressure is any length time sufficient to achieve some decontamination. The sufficient length of time can include, but is not limited to, the range from 10 seconds to 10 minutes.

The use of HPP in combination with one or more forms of $CO_2$ produce several antimicrobial effects to effectively decontaminate non-food materials, such as PPE, and dry/low moisture/low $A_w$ food products. The antimicrobial effects include:

HPP and time under pressure as the primary antimicrobial effect;

HPP and liquid $CO_2$;

HPP and liquid $CO_2$ and carbonic acid; and

HPP and supercritical $CO_2$.

The decontamination process can be achieved through the cumulative effects of HPP and the transitional forms of $CO_2$ mediated by the pressure intensity and the temperature of pressurizing water (outside of packages). In one embodiment, the operating temperature and pressure and sufficient length of time to which the carbon dioxide-filled packages are subjected to is in the range of −20° C. to 35° C. at a pressure from 690 bar to 6,000 bar and a time from 10 seconds to 10 minutes, or any temperature, pressure, and time within or these ranges.

In one embodiment, the operating temperature and pressure and sufficient length of time to which the carbon dioxide-filled packages are subjected to is in the range of 5° C. to 35° C. at a pressure from 690 bar to 6,000 bar and a time from 10 seconds to 10 minutes, or any temperature, pressure, and time within or these ranges.

In one embodiment, the operating temperature and pressure and sufficient length of time to which the carbon dioxide-filled packages are subjected to is in the range of 5° C. to 65° C. at a pressure from 2,000 bar to 10,000 bar or greater and a time from 10 seconds to 10 minutes, or any temperature, pressure, and time within these ranges.

In one embodiment, the operating temperature and pressure and sufficient length of time to which the carbon dioxide-filled packages are subjected to is in the range greater than 65° C. at a pressure greater than 10,000 bar and a time from 10 seconds to 10 minutes.

In one embodiment, the carbon-dioxide-filled packages may undergo a plurality of similar or different cycles of operating temperature, pressure, and time.

When other gases are used as a substitute for or in a mixture with $CO_2$, the temperature and pressure may need to be adjusted to achieve a phase transition to the liquid or supercritical state.

HPP is an isostatic process where pressure is applied uniformly and simultaneously in all directions and is seen in all packages instantaneously regardless of size and geometry. This is different from other decontamination processes where size, geometry and package density determine the length and intensity of the treatment.

The amount of carbon dioxide inside the packages can preferably be any amount that when converted into liquid or supercritical fluid during HPP will result in immersing the product completely, or that will cover the surfaces of the product in liquid or supercritical carbon dioxide.

The amount of the carbon dioxide gas inside the package before undergoing pressurization can range from 10% to 99% by volume of the inside of the package before undergoing pressurization, wherein the remainder of the volume is the product and other gases.

In one embodiment, the volume of carbon dioxide gas inside the package before undergoing pressurization can range from 10% to 90% by volume of the inside of the package before undergoing pressurization.

In one embodiment, the volume of carbon dioxide gas inside the package before undergoing pressurization can range from 25% to 75% by volume of the inside of the package before undergoing pressurization.

One kilogram of carbon dioxide gas, for example, at 1 atm pressure and at a temperature of 25° C. has a volume of about 533 liters. In one embodiment, the ratio of carbon dioxide gas to product can be 50:50 by weight to 75:25 by weight.

Carbon dioxide gas can be essentially pure, meaning the purity is limited to what can be achieved with the gas production method. Carbon dioxide gas can be 99% to 99.999% pure carbon dioxide by weight and the balance is comprised of unavoidable impurities resulting from the method of manufacturing, for example.

As used herein, carbon dioxide gas can include unavoidable impurities from the method of production, including air and water. Some amount of water may be desirable for its ability to form carbonic acid.

HPP can be used on masks and other personal protective equipment and food that has low water activity by packaging the masks or equipment in carbon dioxide gas. Under pressure, $CO_2$ liquifies with some formation of carbonic acid, provided there is some water present. At decompression, most of the $CO_2$ goes back into the gas phase. The residual $CO_2$ will quickly evaporate upon opening of the package. The carbonic acid will not only provide some "moisture" but will be synergistic to HPP.

In one embodiment, the products to be decontaminated can be packaged in a gas already having a low amount of moisture, processed according to HPP, and then dried afterwards. Carbon dioxide gas can be mixed with other gases for use in the packaging of products. In one embodiment, air can be mixed with carbon dioxide gas to constitute 25% by volume of the total air and carbon dioxide gas mixture. The limit of water in air is the saturation point. For example, air can hold 0.022 grams of water per liter of air at 25° C.

A benefit of using air mixed with carbon dioxide gas is that air will normally contain moisture that can lead to the production of carbonic acid during HPP. Air normally comprises water, nitrogen, oxygen, argon, carbon dioxide, neon, helium, methane, krypton, dinitrogen oxide, hydrogen, xenon, ozone, and others. In one embodiment, the package does not need to be provided with any additional water and will rely on any water present in the gas, for example, by combining carbon dioxide with air.

Water, when present in carbon dioxide gas or other carbon dioxide phase can exist as $H_2O$, which can then react with $CO_2$ to yield carbonic acid $H_2CO_3$ and the dissociated ionic form according to the equation.

$$CO_2+H_2O \leftrightarrow H_2CO_3 \leftrightarrow HCO_3^-+H^+$$

For decontamination, the carbon dioxide gas in the packages subjected to HPP will be converted to liquid or supercritical $CO_2$. Depending on the product to be decontaminated, the gas composition, and the operating temperature and pressure, the constituents inside the packages undergoing HPP will change. The volume of the packages will be reduced during HPP, but, gases from air, such as nitrogen and oxygen will not liquify, and will remain in the gas state. The composition of constituents inside of the package being subjected to HPP can be given as weight percents, instead of volume, since weight percents remain the same regardless of the pressure and temperature.

In one embodiment, a high pressure process for decontamination comprises subjecting a hermetically-sealed package containing a product and a gas to an operating pressure by a pressurizing media containing water, wherein the product has a water activity less than or equal to 0.9; increasing the operating pressure to change the gas into a different phase; and maintaining the operating pressure for a sufficient length of time to achieve some decontamination inside the package.

In one embodiment, at least 75% by volume of the gas is selected from the group consisting of carbon dioxide, nitrous oxide, and propane.

In one embodiment, at least 75% by volume of the gas is carbon dioxide.

In one embodiment, at least 99% by volume of the gas is carbon dioxide.

In one embodiment, the gas further comprises one or more gases from the group consisting of air, helium, nitrogen, nitrous oxide, propane, hydrogen, carbon monoxide, and argon.

In one embodiment, the high pressure process comprises producing liquid phase carbon dioxide inside the package when the package is subjected to the operating pressure.

In one embodiment, the high pressure process comprises producing supercritical phase carbon dioxide inside the package when the package is subjected to the operating pressure.

In one embodiment, the carbon dioxide gas comprises carbon dioxide and unavoidable impurities.

In one embodiment, the carbon dioxide gas is mixed with air, wherein air comprises up to 25% of the total volume of combined carbon dioxide and air.

In one embodiment, the air comprises water.

In one embodiment, some or all of the water exists as carbonic acid or its dissociated ionic form.

In one embodiment, at least 99% by volume of contents inside the package before pressurization is comprised of product, carbon dioxide, less than 25% by vol. air of the total gases, water in the air, carbonic acid if water is present, and unavoidable impurities.

In one embodiment, at least 99% by weight of the contents inside the package is comprised of product, carbon dioxide or a mixture of carbon dioxide and air, and unavoidable impurities.

In one embodiment, the mixture of carbon dioxide to air has a ratio in the range of 90:10 to 75:25.

In one embodiment, the product is a personal protective equipment.

In one embodiment, the product is a dry food product having a water activity less than 0.60.

In one embodiment, the product is a food product having a water activity from 0 to 0.9.

In one embodiment, the operating pressure can range from 690 bar to 6,000 bar and the sufficient length of time can range from 10 seconds to 10 minutes.

In one embodiment, a sufficient length of time is at least 10 seconds.

In one embodiment, a high pressure process for decontaminating a product, comprises subjecting a hermetically sealed package that contains at least 99% by weight of the following: product, carbon dioxide as a liquid or supercritical phase, unavoidable impurities, air with or without water, carbonic acid when water is present, to an operating pressure of at least 690 bar for a time of at least 10 seconds, wherein the product has a water activity of less than or equal to 0.9.

In one embodiment, the operating pressure can range from 690 bar to 6,000 bar.

In one embodiment, the product is personal protective equipment.

In one embodiment, the product is a food product.

In one embodiment, the high pressure process further comprises one or more gases from the group consisting of air, helium, nitrogen, hydrogen, carbon monoxide, and argon within the package.

In one embodiment, the high pressure process further comprises nitrous oxide or propane as a liquid within the package.

A matrix for testing both antimicrobial efficacy and PPE integrity is shown in Table 1. The following HPP operating conditions may lead to microbial inactivation.

TABLE 1

Experimental matrix for microbial inactivation and product integrity evaluations.

| Trial** | Pressure (psi) | Time (Mins) | temp (° C.) | $CO_2$ (vol. %) | Air (vol. %) |
|---|---|---|---|---|---|
| Exp 1 | 87000 | 3 | 5 | >90 | <10 |
| Exp 2 | 87000 | 3 | 35 | >90 | <10 |
| Exp 3 | 87000 | 2 | 5 | >90 | <10 |
| Exp 4 | 87000 | 2 | 35 | >90 | <10 |
| | | | | | High humidity air |
| Exp 5 | 87000 | 3 | 5 | 75 | 25 |
| Exp 6 | 87000 | 3 | 35 | 75 | 25 |
| Exp 7 | 87000 | 2 | 5 | 75 | 25 |
| Exp 8 | 87000 | 2 | 35 | 75 | 25 |

Experiment 1-4: gas with 90:10 $CO_2$ to air by vol.

Experiment 5-8: gas with 75:25 $CO_2$ to air by vol.

While illustrative embodiments have been illustrated and described, it will be appreciated that various changes can be made therein without departing from the spirit and scope of the invention.

The invention claimed is:

1. A high pressure process for decontamination, comprising:

introducing a controlled amount of gas into a package with a product and then hermetically sealing the package so as to prevent the controlled amount of gas from escaping as well as preventing water in a pressure vessel from entering the package, wherein the product has no free water;

subjecting, in the pressure vessel, the hermetically-sealed package to an operating pressure by a pressurizing media containing water;

increasing the operating pressure to change the gas into a different phase; and maintaining the operating pressure for a sufficient length of time to achieve some decontamination inside the package.

2. The high pressure process of claim 1, wherein at least 75% by volume of the gas is selected from the group consisting of carbon dioxide, nitrous oxide, and propane.

3. The high pressure process of claim 1, wherein at least 75% by volume of the gas is carbon dioxide.

4. The high pressure process of claim 3, wherein the gas further comprises one or more gases from the group consisting of air, helium, nitrogen, nitrous oxide, propane, hydrogen, carbon monoxide, and argon.

5. The high pressure process of claim 3, comprising producing liquid phase carbon dioxide inside the package when the package is subjected to the operating pressure.

6. The high pressure process of claim 3, comprising producing supercritical phase carbon dioxide inside the package when the package is subjected to the operating pressure.

7. The high pressure process of claim 3, wherein the carbon dioxide gas comprises carbon dioxide and unavoidable impurities.

8. The high pressure process of claim 3, wherein the carbon dioxide gas is mixed with air, wherein air comprises up to 25% of the total volume of combined carbon dioxide and air.

9. The high pressure process of claim 8, wherein the air comprises water, wherein some or all of the water exists as carbonic acid or its dissociated ionic form.

10. The high pressure process of claim 3, wherein at least 99% by volume of contents inside the package before pressurization is comprised of product, carbon dioxide, less than 25% by vol. air of the total gases, water in the air, carbonic acid if water is present, and unavoidable impurities.

11. The high pressure process of claim 3, wherein at least 99% by weight of the contents inside the package is comprised of product, carbon dioxide or a mixture of carbon dioxide and air, and unavoidable impurities.

12. The high pressure process of claim 11, wherein the mixture of carbon dioxide to air has a ratio in the range of 90:10 to 75:25.

13. The high pressure process of claim 1, wherein at least 99% by volume of the gas is carbon dioxide.

14. The high pressure process of claim 1, wherein the product is a personal protective equipment.

15. The high pressure process of claim 1, wherein the operating pressure can range from 690 bar to 6,000 bar and the time can range from 10 seconds to 10 minutes.

16. The high pressure process of claim 1, wherein a sufficient length of time is at least 10 seconds.

17. A high pressure process for decontaminating a product, comprising:

introducing a controlled amount of gas into a package with a product and then hermetically sealing the package so as to prevent the controlled amount of gas from escaping as well as preventing water in a pressure vessel from entering the package, wherein the product has no free water and the hermetically sealed package contains at least 99% by weight of the following: product, carbon dioxide as a liquid or supercritical phase, unavoidable impurities, air with or without water, carbonic acid when water is present;

subjecting, in the pressure vessel, the hermetically sealed package to an operating pressure of at least 690 bar for a time of at least 10 seconds.

18. The high pressure process of claim 17, wherein the operating pressure can range from 690 bar to 6,000 bar.

19. The high pressure process of claim 17, wherein the product is personal protective equipment or a food product.

20. The high pressure process of claim 17, further comprising one or more gases from the group consisting of air, helium, nitrogen, hydrogen, carbon monoxide, and argon within the package.

21. The high pressure process of claim 17, further comprising nitrous oxide or propane as a liquid within the package.

* * * * *